United States Patent
Cho et al.

(10) Patent No.: US 6,954,661 B2
(45) Date of Patent: Oct. 11, 2005

(54) BLOOD SUGAR LEVEL MEASURING APPARATUS

(75) Inventors: Ok-Kyung Cho, Schwerte (DE); Yoon-Ok Kim, Schwerte (DE)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 10/641,262

(22) Filed: Aug. 15, 2003

(65) Prior Publication Data

US 2004/0260165 A1 Dec. 23, 2004

(30) Foreign Application Priority Data

Jun. 23, 2003 (JP) ................................. 2003-178619

(51) Int. Cl.[7] ............................................. A61B 5/00
(52) U.S. Cl. .................. 600/316; 600/322; 600/326
(58) Field of Search ....................... 600/316, 322–323, 600/365, 326

(56) References Cited

U.S. PATENT DOCUMENTS

| | | | |
|---|---|---|---|
| 4,306,569 A | * 12/1981 | Weil et al. ................. 600/549 |
| 4,333,803 A | 6/1982 | Seger | |
| 4,750,140 A | 6/1988 | Asano | |
| 4,802,489 A | 2/1989 | Nitzan | |
| 5,551,422 A | 9/1996 | Simonsen | |
| 5,676,143 A | 10/1997 | Simonsen | |
| 5,725,480 A | * 3/1998 | Oosta et al. ............... 600/310 |
| 5,732,711 A | 3/1998 | Fitzpatrick et al. | |
| 5,743,262 A | 4/1998 | Lepper | |
| 5,769,784 A | * 6/1998 | Barnett et al. ............. 600/300 |
| 5,791,345 A | 8/1998 | Ishihara | |
| 5,795,305 A | 8/1998 | Cho et al. ................. 600/549 |
| 5,924,996 A | 7/1999 | Cho et al. ................. 600/549 |
| 6,226,089 B1 | * 5/2001 | Hakamata ................. 600/319 |
| 6,240,306 B1 | * 5/2001 | Rohrscheib et al. ...... 600/316 |
| 6,266,546 B1 | 7/2001 | Steuer | |
| 6,269,314 B1 | 7/2001 | Iitawaki et al. | |
| 6,280,381 B1 | 8/2001 | Malin | |
| 6,353,226 B1 | 3/2002 | Khalil | |
| 6,615,061 B1 | 9/2003 | Khalil | |
| 2002/0183646 A1 | 12/2002 | Stivoric et al. | |
| 2003/0152133 A1 | 8/2003 | Ellenz | |

FOREIGN PATENT DOCUMENTS

| | | | |
|---|---|---|---|
| EP | 0 778 000 A1 | 6/1997 | |
| JP | 07071945 | 8/1992 | |
| JP | 05317566 | 11/1994 | |
| JP | 06-317566 | 11/1994 | |
| JP | 08322821 | 12/1996 | |
| JP | 10-33512 | 2/1998 | ............ A61B/5/14 |
| JP | 10-108857 | 4/1998 | ............ A61B/5/14 |
| JP | 10-325794 | 12/1998 | .......... G01N/21/35 |

(Continued)

OTHER PUBLICATIONS

R.M. Hillson, et al., "Facial and Sublingual Temperature Changes Following Intravenous Glucose Injection in Diabetics", Diabete & Metabolisme (Paris), 1982, vol. 8, No. 1, pp. 15–19.

A.R. Scott, "Diabetes Mellitus and Thermoregulation", Can. J. Pharmacol. vol. 65, 1987, pp. 1365–1376.

Journal of Medical Association of Thailand, vol. 69, No. 3, 1986, XP–002313054, T. Kanluan.

*Primary Examiner*—Eric F. Winakur
*Assistant Examiner*—Matthew Kremer
(74) *Attorney, Agent, or Firm*—Anntonelli, Terry, Stout & Kraus, LLP

(57) ABSTRACT

Blood sugar levels are measured non-invasively based on temperature measurement. Measured blood sugar levels are corrected using blood oxygen saturation and blood flow volume. The measurement data is further stabilized by taking into consideration the influences of interfering substances on blood oxygen saturation.

19 Claims, 9 Drawing Sheets

FOREIGN PATENT DOCUMENTS

| | | | |
|---|---|---|---|
| JP | 11505451 | 5/1999 | |
| JP | 11155840 | 6/1999 | |
| JP | 11-230901 | 8/1999 | |
| JP | 11318872 | 11/1999 | |
| JP | 10248732 | 3/2000 | |
| JP | 2000 074829 | 3/2000 | |
| JP | 2000506048 | 5/2000 | |
| JP | 2000-258343 | 9/2000 | ......... G01N/21/35 |
| JP | 2002515277 | 5/2002 | |
| JP | 2002535023 | 10/2002 | |
| JP | 2003510556 | 3/2003 | |
| WO | 99/27848 | 6/1999 | ............ A61B/5/00 |
| WO | 00/28887 | 9/2000 | ............ A61B/5/00 |
| WO | WO 01/28414 | 4/2001 | |
| WO | 0128414 | 4/2001 | |
| WO | 01/28417 | 4/2001 | |
| WO | 0187151 | 11/2001 | |
| WO | 03/010510 | 2/2003 | |

\* cited by examiner

BLOOD SUGAR LEVEL MEASURING APPARATUS

BACKGROUND OF THE INVENTION

1. Field of the Invention

The present invention relates to a method and apparatus for non-invasively measuring glucose concentration in a living body without blood sampling.

2. Background Art

Hilson et al. report facial and sublingual temperature changes in diabetics following intravenous glucose injection (non-patent document 1). Scott et al. discuss the issue of diabetes mellitus and thermoregulation (non-patent document 2). Based on such researches, Cho et al. suggest a method and apparatus for determining blood glucose concentration by temperature measurement without requiring the collection of a blood sample (patent document 1 and 2).

Various other attempts have been made to determine glucose concentration without blood sampling. For example, a method has been suggested (patent document 3) whereby a measurement site is irradiated with near-infrared light of three wavelengths, and the intensity of transmitted light as well as the temperature of the living body is detected. Representative values of the second-order differentiated values of absorbance are then calculated, and the representative values are corrected in accordance with the difference of the living body temperature from a predetermined reference temperature. The blood sugar level corresponding to the thus corrected representative values is then determined. An apparatus is also provided (patent document 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (patent document 5) whereby an output ratio between reference light and the light transmitted by an irradiated sample is taken, and then the glucose concentration is calculated by a linear expression of the logarithm of the output ratio and the living body temperature.

Another method for determining the glucose concentration accurately by incorporating corrections is proposed (Patent Document 6). In this method, detection results concerning a plurality of different phenomena, such as infrared absorbance, scattering, and polarimetry, are utilized to determine glucose concentration. In another method, measurements are made in an optical measurement system while removing the influences of component substances other than glucose and making corrections (Patent Document 7). Removal of the influences of irrelevant component substances has been applied to the measurement of not only glucose but also to various other substances. For example, a method has been proposed (Patent Document 8) for removing the influence of irrelevant component substances when measuring the oxygen consumption amounts or oxygen contents in human bodies.

(Non-Patent document 1)
R. M. Hilson and T. D. R. Hockaday, "Facial and sublingual temperature changes following intravenous glucose injection in diabetics," Diabete & Metabolisme, 8, pp. 15–19: 1982

(Non-Patent Document 2)
A. R. Scott, T. Bennett, I. A. MacDonald, "Diabetes mellitus and thermoregulation," Can. J. Physiol. Pharmacol., 65, pp. 1365–1376: 1987

(Patent Document 1)
U.S. Pat. No. 5,924,996
(Patent Document 2)
U.S. Pat. No. 5,795,305
(Patent Document 3)
JP Patent Publication (Kokai) No. 2000-258343 A
(Patent Document 4)
JP Patent Publication (Kokai) No. 10-33512 A (1998)
(Patent Document 5)
JP Patent Publication (Kokai) No. 10-108857 A (1998)
(Patent Document 6)
JP Patent Publication (Kohyo) No. 2001-524342 A
(Patent Document 7)
JP Patent Publication (Kokai) No. 10-325794 A (1998)
(Patent Document 8)
JP Patent Publication (Kohyo) No. 2003-517342 A Glucose (blood sugar) in the blood is used for glucose oxidation reaction in cells to produce necessary energy for the maintenance of living bodies. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also varies due to factors other than blood glucose concentration. While methods have been proposed to determine blood glucose concentration by temperature measurement without blood sampling, they lack sufficient accuracy.

Methods of determining glucose concentrations based on the intensity of transmitted light, such as near-infrared, have also been devised. However, it is difficult to perform accurate analysis using these methods because the identities of the absorbance peaks of near-infrared light are unclear. In order to solve this problem, correction techniques have been proposed that aim to remove interfering substances in an optical measurement system, but none of them are accurate enough to be practical.

SUMMARY OF THE INVENTION

It is the object of the invention to provide a method and apparatus for determining blood glucose concentration with high accuracy based on temperature data of the subject without blood sampling.

Blood sugar is delivered to the cells throughout the human body via blood vessel systems, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The volume of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. On the assumption that the body temperature is determined by the balance between the amount of energy produced in the body by glucose burning, namely heat production, and heat dissipation such as mentioned above, the inventors set up the following model:

(1) The amount of heat production and the amount of heat dissipation are considered equal.
(2) The amount of heat production is a function of the blood glucose concentration and the volume of oxygen supply.

(3) The volume of oxygen supply is determined by the blood hemoglobin concentration, the blood hemoglobin oxygen saturation, and the volume of blood flow in the capillary blood vessels.

(4) The amount of heat dissipation is mainly determined by heat convection and heat radiation.

According to this model, we achieved the present invention after realizing that blood sugar levels can be accurately determined on the basis of the results of measuring the temperature of the body surface and measuring parameters relating to the blood oxygen concentration and the blood flow volume. The parameters can be measured from a part of the human body, such as the fingertip. The parameters relating to convection and radiation can be determined by carrying out thermal measurements on the fingertip. The parameters relating to the blood hemoglobin concentration and the blood hemoglobin oxygen saturation can be determined by spectroscopically measuring the blood hemoglobin and then finding the ratio between the hemoglobin bound with oxygen and the hemoglobin not bound with oxygen. However, spectroscopic measurement is influenced by interfering substances, so it is necessary to correct for the interfering substances. This can be achieved by measuring the bilirubin and turbidity in blood, melanin pigment in the epidermis, and the thickness and roughness of the skin, which are major interfering substances when spectroscopically measuring a part of the human body. The parameter relating to the volume of blood flow can be determined by measuring the amount of heat transfer from the skin.

In one aspect, the invention provides a blood sugar level measuring apparatus including (1) a heat amount measuring unit for measuring a plurality of temperatures derived from the body surface. The resultant information is used for calculating the amount of convective heat transfer and the amount of radiation heat transfer constituting the dissipation of heat from the body surface. The apparatus also includes (2) a blood flow volume measuring unit for obtaining information concerning the volume of blood flow. It also includes (3) an optical measuring unit for obtaining the hemoglobin concentration and hemoglobin oxygen saturation in blood. This unit includes a light source for generating light of at least three different wavelengths, an optical system for irradiating the body surface with light emitted by the light source, and at least three different photodetectors for detecting the light that has been shone on the body surface. The apparatus further includes (4) a storage unit for storing the relationships between the individual parameters corresponding to the multiple temperatures, blood flow volume, hemoglobin concentration and hemoglobin oxygen saturation in blood, and blood sugar levels. It also includes (5) a computing unit for converting the measurement values provided by the heat amount measuring unit, the blood flow volume measuring unit, and the optical measuring unit into parameters. The computing unit also computes a blood sugar level by applying the parameters to the relationships stored in the storage unit. The apparatus further includes (6) a display unit for displaying the blood sugar level computed by the computing unit. Preferably, the photodetectors include a first photodetector for detecting light reflected by the body surface, a second photodetector for detecting light scattered by the body surface, and a third photodetector for detecting light that has penetrated into the skin through the body surface and that has exited from the body surface. Preferably, the optical measuring unit measures the blood hemoglobin concentration and hemoglobin oxygen saturation by compensating for the influences of bilirubin, turbidity in blood, melanin pigment, the roughness of the skin surface, and the thickness of the skin using three or more, preferably five, wavelengths.

In another aspect, the invention provides a blood sugar level measuring apparatus including an ambient temperature detector for measuring the ambient temperature, a body-surface contact unit to be brought into contact with a body surface, a radiation temperature detector for measuring the radiation heat from the body surface, and an adjacent-temperature detector disposed adjacent to the body-surface contact unit. The apparatus also includes an indirect-temperature detector for detecting the temperature at a position distanced away from the body-surface contact unit, a heat conducting member connecting the body-surface contact unit with the indirect-temperature detector, and a light source for producing light of at least three different wavelengths consisting of 810 nm, 950 nm, and a third wavelength. It also includes an optical system for irradiating the body surface with the light emitted by the light source and at least three different photodetectors for detecting the light with which the body surface has been irradiated. It further includes a storage unit for storing the relationships between the individual outputs from the ambient temperature detector, radiation temperature detector, adjacent-temperature detector, indirect-temperature detector and the at least three different photodetectors, and blood sugar levels. The apparatus further includes a computing unit for calculating a blood sugar level using the individual outputs while referring to the relationships stored in the storage unit. The apparatus also includes a display unit for displaying the blood sugar level calculated by the computing unit.

In accordance with the invention, blood sugar levels can be determined non-invasively with an accuracy similar to that according to the invasive methods according to the prior art.

DESCRIPTION OF THE PREFERRED EMBODIMENTS

The invention will now be described by way of preferred embodiments thereof with reference made to the drawings.

Initially, the above-mentioned model will be described in more specific terms. Regarding the amount of heat dissipation, convective heat transfer, which is one of the main causes of heat dissipation, is related to temperature difference between the ambient (room) temperature and the body-surface temperature. Another main cause of dissipation, namely the amount of heat dissipation due to radiation, is proportional to the fourth power of the body-surface temperature according to the Stefan-Boltzmann law. Thus, it can be seen that the amount of heat dissipation from the human body is related to the room temperature and the body-surface temperature. On the other hand, the oxygen supply, which is a major factor related to the amount of heat production, is expressed as the product of hemoglobin concentration, hemoglobin oxygen saturation, and blood flow volume.

The hemoglobin concentration can be basically measured by the absorbance of the wavelength at which the molar absorbance coefficient of the oxy-hemoglobin is equal to that of the deoxy-hemoglobin (equal-absorbance wavelength). The hemoglobin oxygen saturation can be basically measured by measuring the absorbance of the equal-absorbance wavelength and the absorbance of at least one different wavelength at which the ratio between the molar absorbance coefficient of the oxy-hemoglobin and that of the deoxy-hemoglobin is known, and then solving simultaneous equations. However, in order to accurately determine the hemoglobin concentration and hemoglobin oxidation saturation by absorbance, the influence of interfering components must be corrected. The interfering components affecting the absorbance include the roughness of the skin surface, the thickness of the skin (epidermis), the color of the skin, and other interfering components in blood. These interfering components can be measured in various manners, of which one example will be described below.

The roughness of the skin surface can be measured by comparing reflected light (specular reflection) with scattered light on the skin surface. When the skin surface is smooth like that of the mirror surface, the reflected light would be stronger and little scattered light would be observed. On the contrary, when the skin surface is rough, the difference between the reflected light and the scattered light would be smaller. Thus, by determining the ratio between the reflected light and the scattered light that have been detected, the roughness of the skin surface can be estimated.

Figure 1:
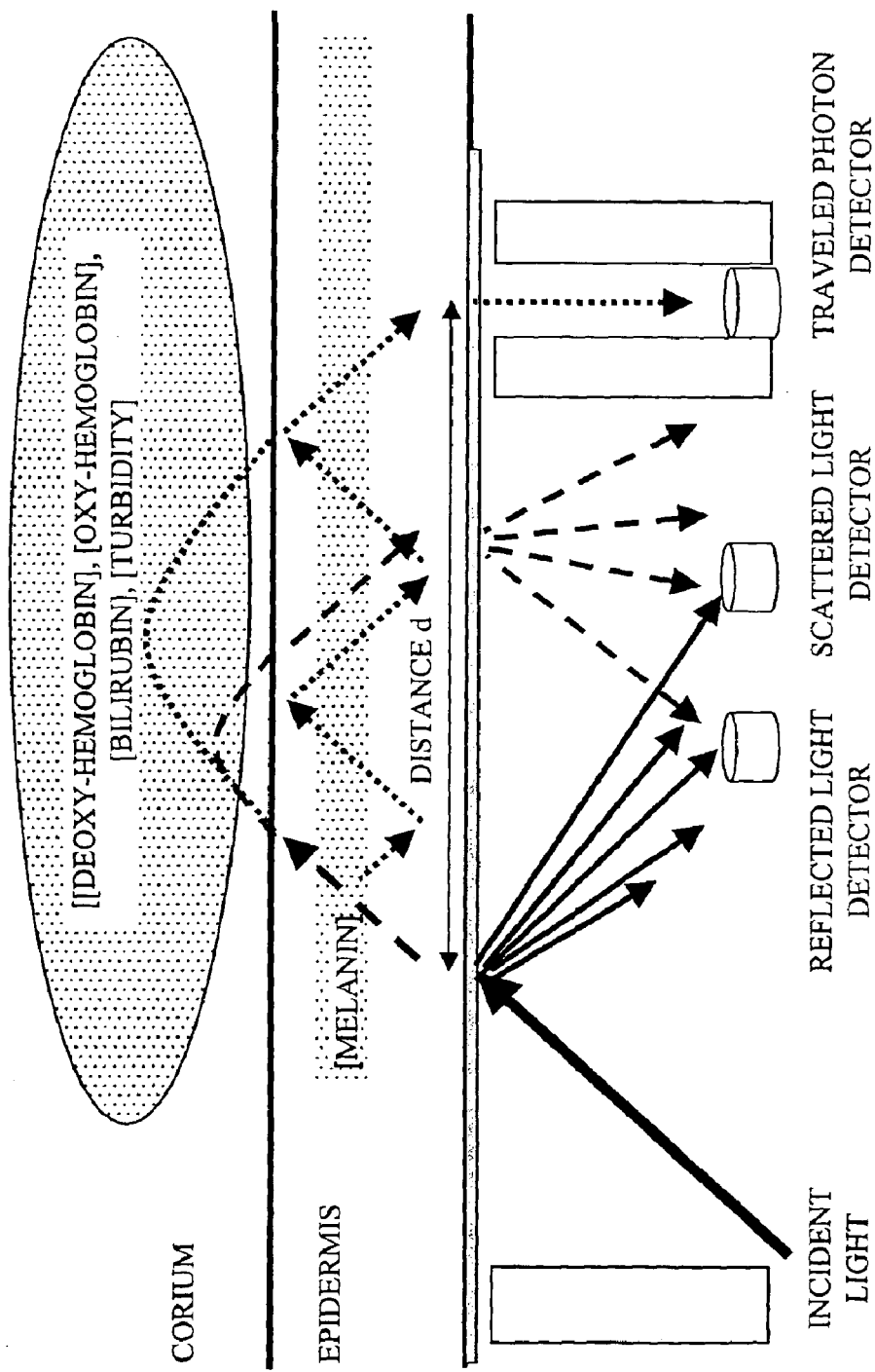
FIG. 1 shows a model of the transmission of light in the case of irradiating the skin surface with continuous light.

The thickness of the skin can be measured by measuring the intensity of the light that has traveled in the skin by a distance d. FIG. 1 shows the behavior of the light in the case where the skin surface was irradiated with continuous light. As the light of a certain wavelength and intensity is irradiated, the light is reflected and scattered by the skin surface. Part of the light penetrates the skin and experiences scatterings and diffusion in a repeated manner. In such a behavior of light, the depth of penetration of the light that has traveled by distance d is substantially constant depending on the wavelength. The skin does not contain blood, so it has a low fluidity, resulting in a low absorbance. On the other hand, the corium contains blood and therefore has a high fluidity, resulting in a high absorbance. Thus, when the skin is thin, the light can penetrate deeper into the corium, resulting in a larger absorbance. When the skin is thick, the distance traveled by the light becomes shorter, so that the absorbance becomes smaller. By taking the ratio between the intensity of light that has traveled distance d and the intensity of the light that has traveled in a standard substance with a known thickness in the same manner, the thickness of the skin can be estimated.

The color of the skin can be determined by the absorption spectrum of the melanin pigment.

There are two major kinds of interfering components in blood. One is bilirubin, which is one of the causative agents for icteric symptoms. The other is turbidity, which is one of the causative agents for hyperlipemia. The concentrations of these components can also be determined by their absorption spectra.

Thus, the hemoglobin concentration and the hemoglobin oxygen saturation can be determined by carrying out absorbance measurements at at least two wavelengths at which the ratio of molar absorbance coefficients between the oxy-hemoglobin and the deoxy-hemoglobin is equal or known, and three wavelengths at which the molar absorbance of melanin pigment, bilirubin and turbidity is known. The measurements are carried out using at least three detectors, namely a reflected light detector for detecting mainly reflected light, a scattered light detector for detecting mainly scattered light, and a traveled photon detector for detecting traveled photon.

The reflected light detector can detect part of the scattered light produced by the light passing inside the body and then exiting from the body surface, as well as detecting mainly the reflected light reflected by the body surface. Accordingly, the ratio between the reflected light and scattered light that have been detected can be taken, so that the roughness of the skin surface can be estimated. The scattered light detector can detect part of the reflected light reflected from the body surface, as well as detecting mainly the scattered light produced by the light passing inside the body and then exiting through the body surface. Accordingly, an appropriate absorbance measurement can be made regarding the hemoglobin concentration, hemoglobin oxygen saturation, melanin pigment, bilirubin, and/or turbidity. The paths of the traveled photon to the traveled photon detector are optically blocked so that the light derived from reflected light and scattered light is not detected by the traveled photon detector. Thus, the traveled photon detector can detect only traveled photon, so that the skin thickness can be estimated. During detection, a total of at least three detectors, namely at least one each of the reflected light detector, scattered light detector, and traveled photon detector, are used. Preferably, additional detectors with similar functions and with higher detection sensitivities depending on the kind of wavelength may be used. Further, a transmitted light detector may be added for detecting light that has passed through the detection area, as necessary. In that case, the measurement accuracy can be improved by capturing pulsation in blood.

The wavelength values described herein are most appropriate values for obtaining absorbance for intended purposes, such as for obtaining the absorbance at the equal molar absorbance coefficients, or for obtaining the peak of absorbance. Thus, wavelengths close to those described herein may be used for similar measurements.

The rest is the blood flow volume, which can be measured by various methods. One example will be described below.

Figure 2:
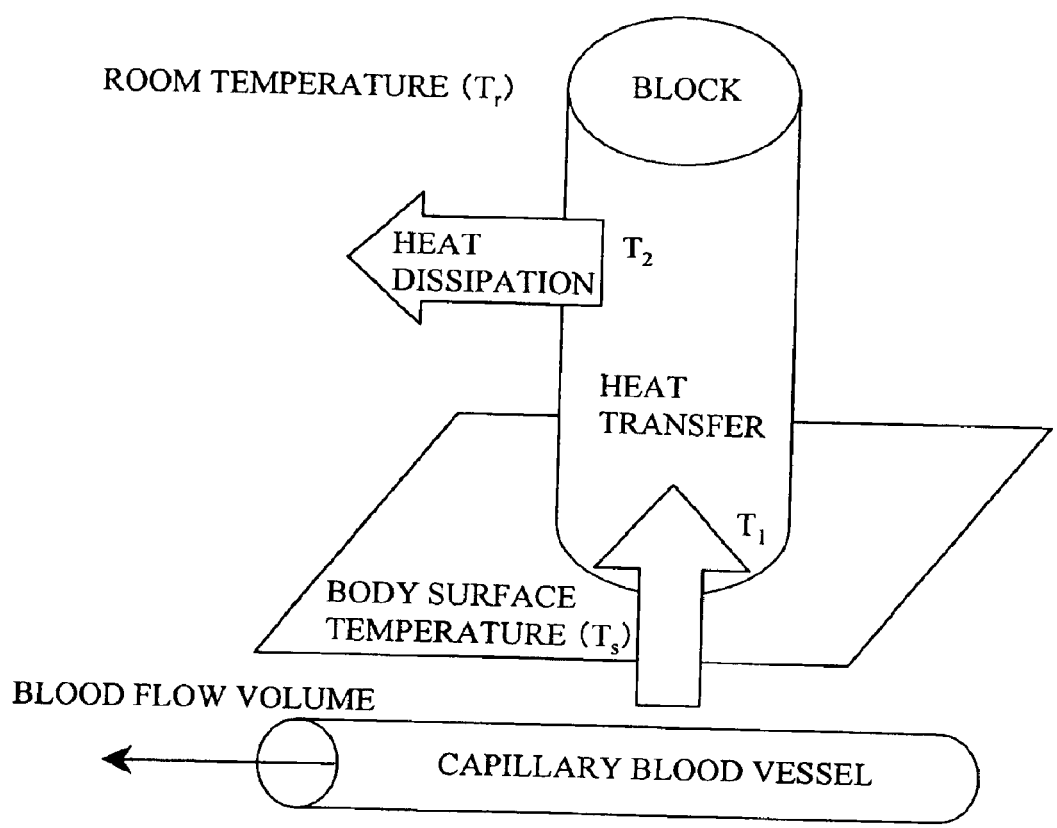
FIG. 2 shows a model of heat transfer from the body surface to a block.

FIG. 2 shows a model for the description of the transfer of heat from the body surface to a solid block having a certain heat capacity when the block is brought into contact with the body surface for a certain time and then separated. The block is made of resin such as plastic or vinyl chloride. In the illustrated example, attention will be focused on the chronological variation of the temperature $T_1$ of a portion of the block in contact with the body surface, and the chronological variation of the temperature $T_2$ of a point on the block away from the body surface. The blood flow volume can be estimated by monitoring mainly the chronological variation of the temperature $T_2$ (of the spatially separated point on the block). The details will follow.

Before the block comes into contact with the body surface, the temperatures $T_1$ and $T_2$ at the two points of the block are equal to the room temperature $T_r$. When a body-surface temperature $T_s$ is higher than the room temperature $T_r$, the temperature $T_1$ swiftly rises due to the transfer of heat from the skin as the block comes into contact with the body surface, and it approaches the body-surface temperature $T_s$. On the other hand, the temperature $T_2$ is less than the temperature $T_1$ as the heat conducted through the block is dissipated from the block surface, and it rises more gradually than the temperature $T_1$. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the heat transfer coefficient from the capillary blood vessels to the surrounding cell tissues is given as a function of the blood flow volume. Thus, by measuring the amount of heat transfer from the body surface to the block by monitoring the chronological variation of the temperatures $T_1$ and $T_2$, the amount of heat transferred from the capillary blood vessels to the cell tissues can be estimated. Based on this estimation, the blood flow volume can then be estimated. Accordingly, by monitoring the temperature changes in the $T_1$ and $T_2$ chronologically and thus measuring the amount of heat transfer from the body surface to the block, the amount of heat transfer from the capillary blood vessels to the cell tissues can be estimated. Based on this estimation, the blood flow volume can be estimated.

Figure 3:
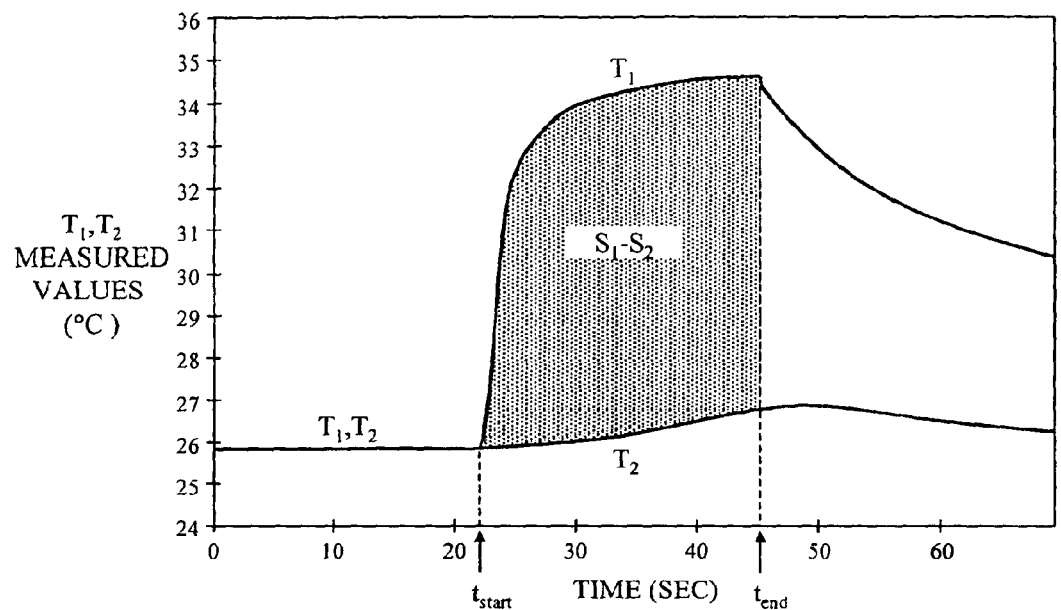
FIG. 3 plots the measurement values of temperatures $T_1$ and $T_2$ as they change with time.

FIG. 3 shows the chronological variation of the measured values of the temperature $T_1$ at the portion of the block in contact with the body surface and the temperature $T_2$ at the position on the block away from the body-surface contact position. As the block comes into contact with the body surface, the $T_1$ measured value swiftly rises, and it gradually drops as the block is brought out of contact.

Figure 4:
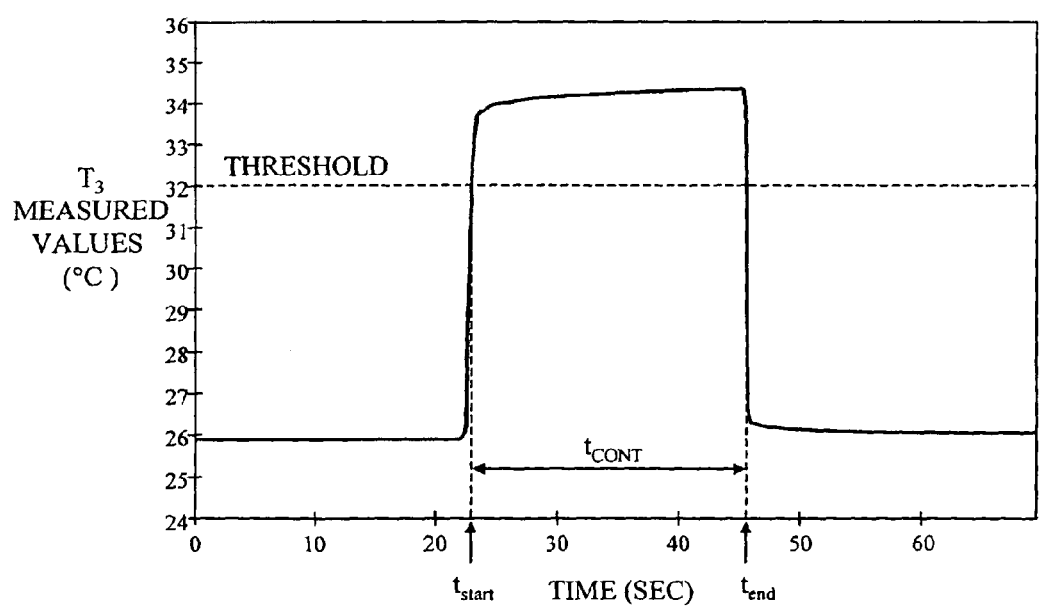
FIG. 4 shows an example of measuring the chronological change in temperature $T_3$.

FIG. 4 shows the chronological variation of the measured value of the temperature $T_3$ measured by a radiation temperature detector. As the detector detects the temperature due to the radiation from the body surface, it is more sensitive to temperature changes than other sensors. Because radiation heat propagates as an electromagnetic wave, it can transmit temperature changes instantaneously. Thus, by locating the radiation temperature detector near where the block contacts the body surface to measure radiated heat, as shown in FIG. 8 (which will be described later), the time of start of contact $t_{start}$ between the block and the body surface and the time of end of contact $t_{end}$ can be detected by changes in the temperature $T_3$. For example, a temperature threshold value is set as shown in FIG. 4. The contact start time $t_{start}$ is when the temperature threshold value is exceeded. The contact end time $t_{end}$ is when the temperature $T_3$ drops below the threshold. The temperature threshold is set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining coefficients a, b, c, and d by the non-linear least-squares method. For the resultant approximate expression, T is integrated between time $t_{start}$ and time $t_{end}$ to obtain a value $S_1$.

Similarly, an integrated value $S_2$ is calculated from the $T_2$ measured value. The smaller $(S_1-S_2)$, the larger the amount of transfer of heat from the finger surface to the position of $T_2$. $(S_1-S_2)$ becomes larger with increasing finger contact time $t_{cont}$ $(=t_{end}-t_{start})$. Thus, $a_5/(t_{cont} \times (S_1-S_2))$ is designated as a parameter $x_5$ indicating the volume of blood flow, where $a_5$ is a proportionality coefficient.

Thus, it will be seen that the measured amounts necessary for the determination of blood glucose concentration by the above-described model are the room temperature (ambient temperature), body surface temperature changes, temperature changes in the block brought into contact with the body surface, the temperature due to radiation from the body surface, and the absorbance of reflected light or scattered light, and the intensity of traveled photon, with respect to at least three wavelengths.

Figure 5:
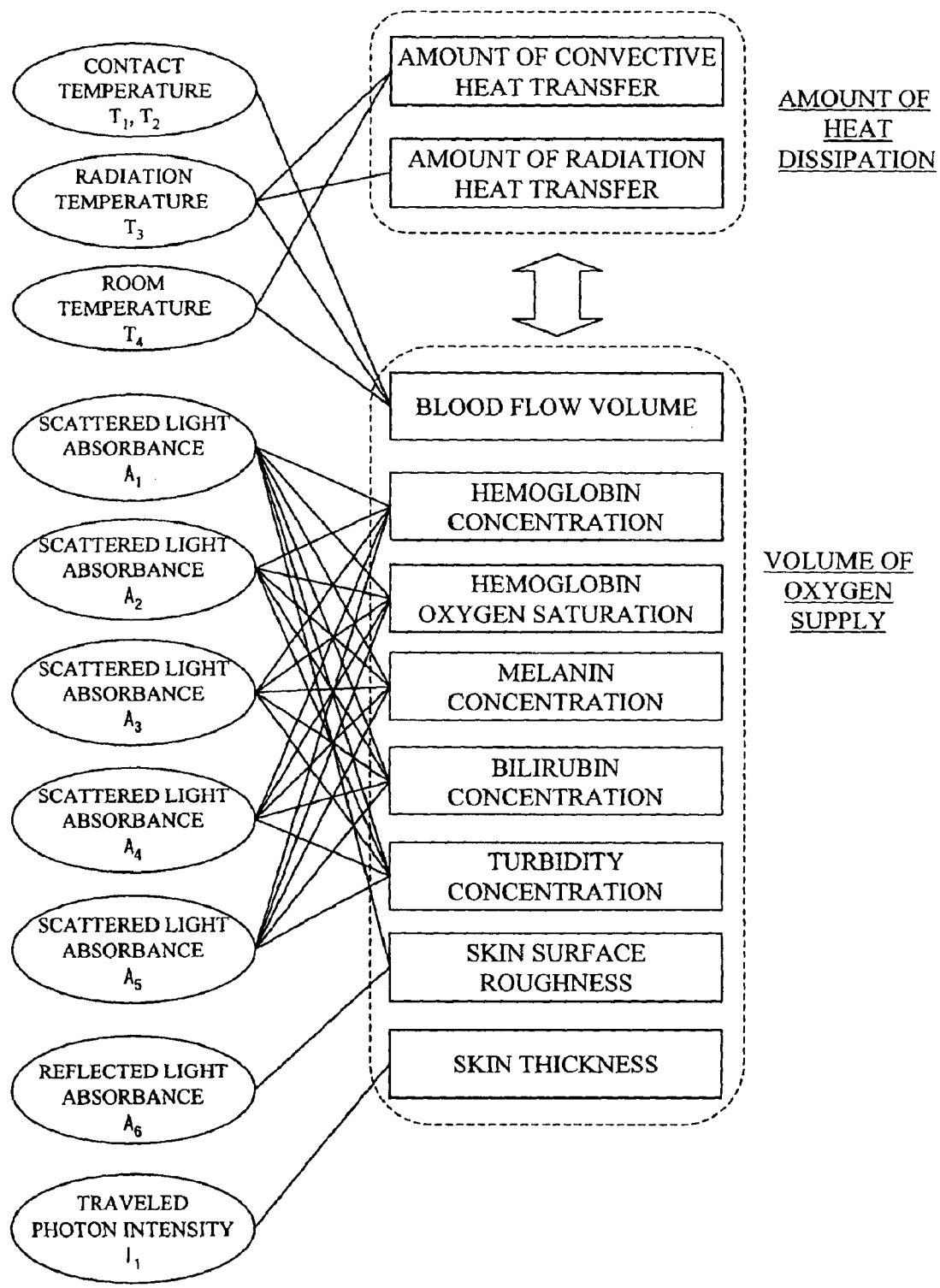
FIG. 5 shows the relationships between measurement values provided by various sensors and the parameters derived therefrom.

FIG. 5 shows the relationships between the measured values provided by various sensors and the parameters derived therefrom. A block is brought into contact with the body surface, and chronological changes in two kinds of temperatures $T_1$ and $T_2$ are measured by two temperature sensors provided at two locations of the block. Separately, a radiation temperature $T_3$ on the body surface and the room temperature $T_4$ are measured. Absorbance $A_1$ and $A_2$ of scattered light are measured at at least two wavelengths related to the absorbance of hemoglobin. Absorbance $A_3$, $A_4$, and $A_5$ of reflected light is measured at at least three wavelengths related to the absorbance of bilirubin, turbidity, and melanin. Absorbance $A_6$ of the reflected light is separately measured at at least one wavelength. Alternatively, the absorbance of the reflected light may be measured by the above-mentioned five different wavelengths, so that their mean or median value can be used. The intensity $I_1$ of traveled photon is measured at at least one wavelength. Alternatively, the intensity may be measured by the five different wavelengths, so that their mean or median value can be used. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. The absorbance $A_1$ to $A_6$ and intensity $I_1$ provide parameters related to the hemoglobin concentration and the hemoglobin oxygen saturation.

Hereafter, an example of apparatus for non-invasively measuring blood sugar levels according to the principle of the invention will be described.

Figure 6:
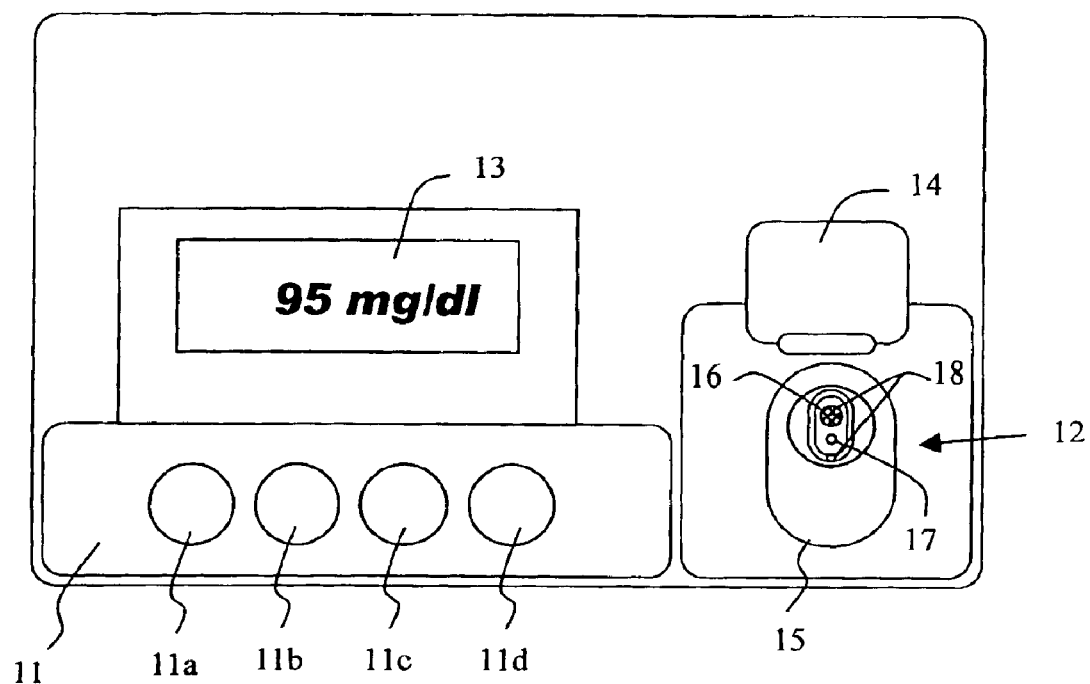
FIG. 6 shows an upper plan view of a non-invasive blood sugar level measuring apparatus according to the present invention.

FIG. 6 shows a top plan view of the non-invasive blood sugar level measuring apparatus according to the invention. While in this example the skin on the ball of the finger tip is used as the body surface, other parts of the body surface may be used.

On the top surface of the apparatus are provided an operation unit 11, a measuring unit 12 where the finger to be measured is to be placed, and a display unit 13 for displaying measurement results, the state of the apparatus, measured values, for example. The operation unit 11 includes four push buttons 11a to 11d for operating the apparatus. The measuring unit 12 has a cover 14 which, when opened (as shown), reveals a finger rest 15 with an oval periphery. The finger rest 15 accommodates an opening end 16 of a radiation temperature sensor, a contact temperature sensor 17, and an optical sensor 18.

Figure 7:
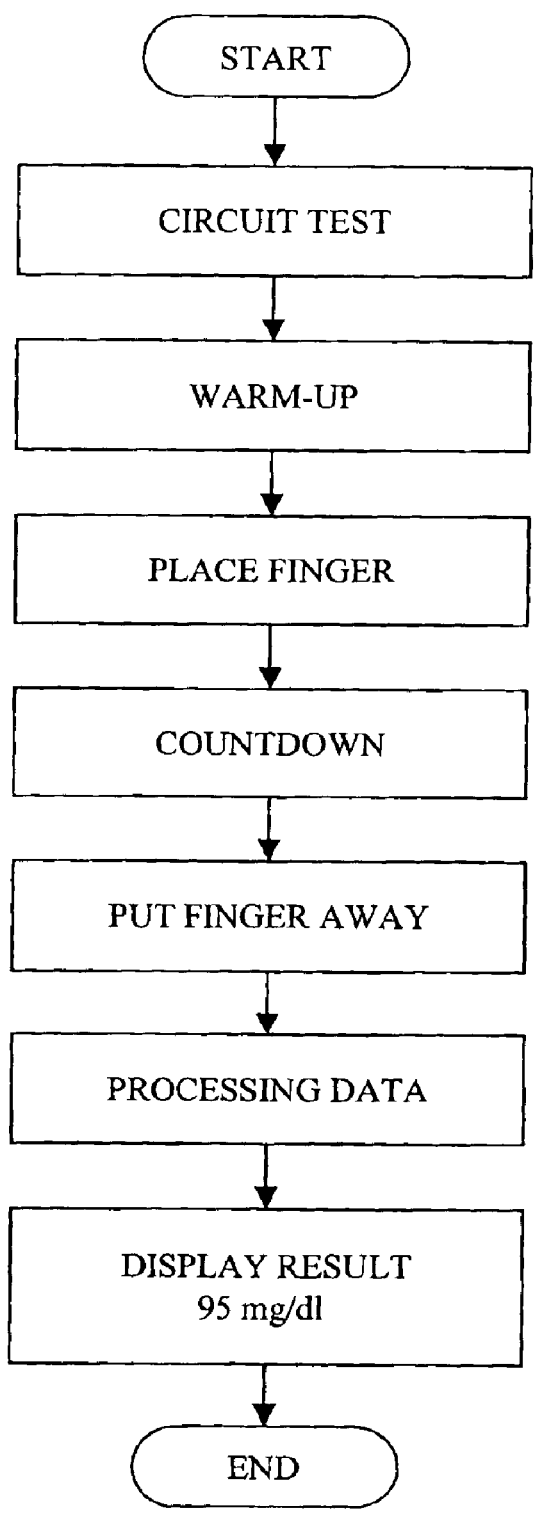
FIG. 7 shows the operating procedure for the apparatus.

FIG. 7 shows the procedure for operating the apparatus. As one of the buttons on the operation unit is depressed to turn on the apparatus, an indication "Warming up" is displayed on the LCD while the electronic circuits in the apparatus are being warmed up. At the same time, a check program is activated to automatically check the electric circuits. As the warm-up phase is over, an indication "Place your finger" appears on the LCD. As the user places his or her finger on the finger rest, counting down begin on the LCD. When the countdown is over, an indication "Put your finger away" appears on the LCD. As the user follows the instruction, the LCD indicates "Processing data." Thereafter, the display shows the blood sugar level, which is then stored in an IC card together with the date and time. After the user took notes of the displayed blood sugar level, he or she pushes another button on the operation unit. About one minute later, the apparatus displays a message "Place your finger" on the LCD, thus indicating that the apparatus is ready for the next cycle of measurement.

FIG. 8 shows the measuring unit in detail. In FIG. 8, (a) is a top plan view, (b) is a cross section taken along line X—X of (a), (c) is a cross section taken along line Y—Y of (a), and (d) is a cross section taken along Z—Z of (a).

First, the process of measuring temperatures by the non-invasive blood sugar level measuring apparatus according to the invention will be described. In the portion of the measuring unit where the object of measurement (ball of the finger) is to come into contact, a thin plate 21 of a highly heat-conductive material, such as gold, is placed. A bar-shaped heat-conductive member 22 made of material such as polyvinylchloride whose heat conductivity is lower than that of the plate 21 is thermally connected to the plate 21 and extends into the apparatus. The temperature sensors include a thermistor 23 for measuring the temperature of the plate 21 and acting as an adjacent-temperature detector with respect to the measured object. There is also a thermistor 24 for measuring the temperature of the heat-conducting member away from the plate 21 by a certain distance and acting as an indirect-temperature detector with respect to the measured object. An infrared lens 25 is disposed inside the apparatus at such a position that the measured object (ball of the finger) placed on the finger rest 15 can be seen through the lens. Below the infrared lens 25 is disposed a pyroelectric detector 27 via an infrared radiation-transmitting window 26. Another thermistor 28 is disposed near the pyroelectric detector 27.

Thus, the temperature sensor portion of the measuring unit has four temperature sensors, and they measure four kinds of temperatures as follows:
(1) Temperature on the finger surface (thermistor 23): $T_1$
(2) Temperature of the heat-conducting member (thermistor 24): $T_2$
(3) Temperature of radiation from the finger (pyroelectric detector 27): $T_3$
(4) Room temperature (thermistor 28): $T_4$ The optical sensor 18 measures the hemoglobin concentration and the hemoglobin oxygen saturation necessary for the determination of the oxygen supply volume. In order to measure the hemoglobin concentration and the hemoglobin oxygen saturation accurately, it is necessary to measure the absorbance of scattered light at at least five wavelengths, the absorbance of reflected light at at least one wavelength, and the intensity of traveled photon at at least one wavelength. The accuracy of the absorbance of reflected light can be improved by measuring at a plurality of wavelengths, if possible, and then using a mean value. Thus, in the present embodiment, the absorbance of reflected light is measured at five different wavelengths. The accuracy of the measurement of the intensity of traveled photon can also be improved by measuring at a plurality of wavelengths, if possible, and then using a mean value. Thus, in the present embodiment, the intensity of traveled photon is measured at two wavelengths in the near-infrared wavelength region. FIG. 8 shows a configuration for carrying out the measurement using five light sources 35a to 35e and three detectors 36 to 38.

Figure 8A:
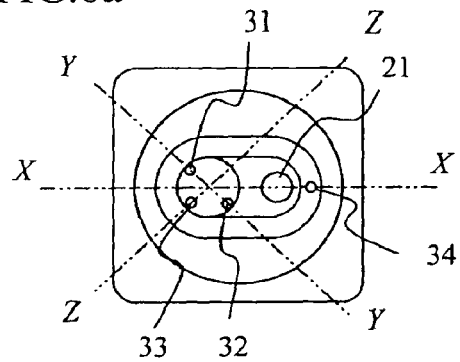
FIG. 8 shows the measuring unit in detail.
Figure 8B:
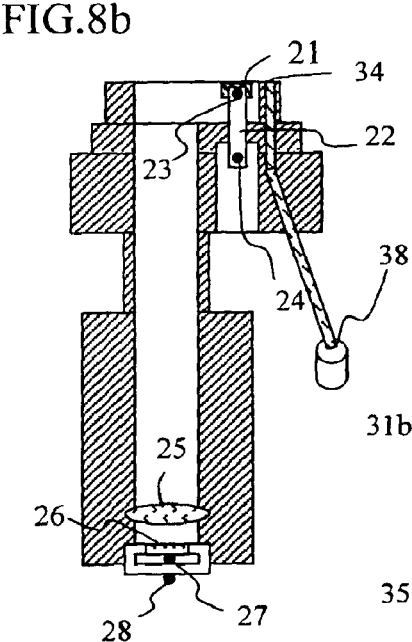
Figure 8C:
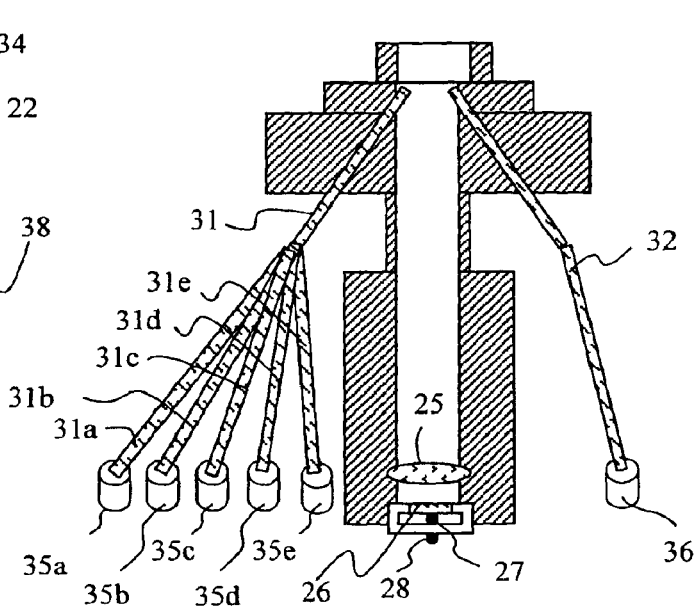
Figure 8D:
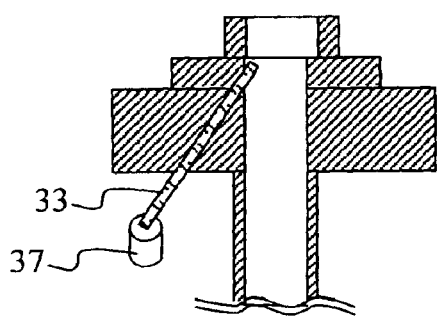

The ends of four optical fibers 31 to 34 are located in the optical sensor 18. The optical fiber 31 is for optical irradiation, while the optical fibers 32 to 34 are for receiving light. As shown in FIG. 8(c), the optical fiber 31 connects to branch fibers 31a to 31e that are provided with light-emitting diodes 35a to 35e of five wavelengths at the respective ends thereof. The other end of the light-receiving optical fiber 32 is provided with a photodiode 36. The other end of the light-receiving optical fiber 33 is provided with a photodiode 37. The other end of the light-receiving optical fiber 34 is provided with a photodiode 38. The light-emitting diode 35a emits light with a wavelength of 810 nm, while the light-emitting diode 35b emits light with a wavelength of 950 nm. The wavelength 810 nm is the equal absorbance wavelength at which the molar absorbance coefficient of the oxy-hemoglobin is equal to that of the deoxy-hemoglobin. The wavelength 950 nm is the wavelength at which the difference between the molar absorbance coefficient of the oxy-hemoglobin and that of the deoxy-hemoglobin is large. The light-emitting diode 35c emits light with wavelength 520 nm, at which the molar absorbance coefficient of melanin is large. The light-emitting diode 35d emits light with wavelength 450 nm, at which the molar absorbance coefficient of bilirubin is large. The light-emitting diode 35e emits light with wavelength 660 nm, at which the molar absorbance coefficient of turbidity is large.

The five light-emitting diodes 35a to 35e emit light in a time-sharing manner. The finger of the subject is irradiated with the light emitted by the light-emitting diodes 35a to 35e via the irradiating optical fiber 31. The light shone on the finger is reflected by the skin, enters the light-receiving optical fiber 32, and is eventually detected by the photodiode 36. The scattered light enters the light-receiving optical fiber 33 and is then detected by the photodiode 37. The traveled photon enters the light-receiving optical fiber 34 and is then detected by the photodiode 38. These light-receiving optical fibers have a light-blocking structure such that they can prevent the direct entry of reflected and/or scattered light.

As the light with which the skin of the finger is irradiated is reflected by the skin, part of the light is scattered in all directions due to the roughness of the skin surface. The reflected light is measured by the photodiode 36 and part of the scattered light is measured by the photodiode 37. As the light with which the finger is irradiated is reflected or scattered by the finger skin, part of the light penetrates the skin and enters into the tissues and is then absorbed by the melanin pigment contained in the epidermis, by the hemoglobin in the blood flowing in the capillary blood vessels, and by the interfering substances such as bilirubin and turbidity. The measurement data provided by the photodiodes 36 and 37 has reflectance R, and the absorbance can be approximately calculated by log(1/R). The finger is thus irradiated with light with the wavelengths of 450 nm, 520 nm, 660 nm, 810 nm, and 950 nm, and R is measured for each and also log(1/R) is calculated for each. Thus, absorbance $A_{D11}$, and $A_{D21}$ for wavelength 450 nm, absorbance $A_{D12}$ and $A_{D22}$ for wavelength 520 nm, absorbance $A_{D13}$ and $A_{D23}$ for wavelength 660 nm, absorbance $A_{D14}$ and $A_{D24}$ for wavelength 810 nm, and absorbance $A_{D15}$ and $A_{D25}$ for wavelength 950 nm, respectively, are measured. (The reflected light absorbance of wavelength $\lambda_i$ detected by the photodiode 36 is indicated by $A_{D1i}$. The scattered-light absorbance detected by the photodiode 37 is indicated by $A_{D2i}$. And the traveled photon intensity detected by the photodiode 38 is indicated by $I_{D3i}$.)

Part of the light penetrates into the finger through the epidermis, experiences repeated scatterings inside, and travels a certain distance d. The thus traveled photon is then measured by the photodiode 38.

When the deoxy-hemoglobin concentration is [Hb], the oxy-hemoglobin concentration is [HbO$_2$], the bilirubin concentration is [Bi], the turbidity concentration is [Tur], and the melanin pigment concentration is [Me], scattered-light absorbance $A_{D2i}$ of wavelength $\lambda_i$ is expressed by the following equations:

$$A_{D2i} = a\{[Hb] \times A_{Hb}(\lambda i) + [HbO_2] \times A_{HbO_2}(\lambda i) + [Bi] \times A_{Bi}(\lambda i) + [Tur] \times A_{Tur}(\lambda i) + [Me] \times A_{Me}(\lambda i)\} \times D \times a_{Rough}$$

$$a_{Rough} = \frac{b \times \sum A_{D2i}}{\sum A_{D1i}}, D = \frac{1}{c \times \sum_i I_{D3i}}$$

where $A_{Hb}(\lambda_i)$, $A_{HbO2}(\lambda_i)$, $A_{Bi}(\lambda_i)$, $A_{Tur}(\lambda_i)$, and $A_{Me}(\lambda_i)$ are the molar absorbance coefficients of the deoxy-hemoglobin, the oxy-hemoglobin, bilirubin, turbidity, and melanin, respectively, and are known at the respective wavelengths. Terms a, b, and c are proportionality coefficients. $A_{D1i}$ is the reflected-light absorbance of wavelength $\lambda_i$, and $I_{D3i}$ is the traveled photon intensity of wavelength $\lambda_i$. From the above equations, the parameter $a_{Rough}$ of the roughness of the skin surface and the parameter D of the skin thickness can be determined as constants, and can be substituted in the equation of $A_{D2i}$. The parameter relating to the thickness of the skin can be determined from the measurement value obtained by the traveled photon detector, so that the influence of the thickness of the skin can be corrected. Since i=1 to 5, five equations of $A_{D2i}$ are produced. By solving these simultaneous equations, the five variables to be obtained, namely [Hb], [HbO$_2$], [Bi], [Tur], and [Me], can be obtained. The hemoglobin concentration [Hb]+[HbO$_2$], and the hemoglobin oxygen saturation [HbO$_2$]/([Hb]+[HbO$_2$]) can be determined from the above-obtained [Hb] and [HbO$_2$].

In the present example, the hemoglobin concentration and the hemoglobin oxygen saturation are measured by measuring absorbance at five wavelengths. Preferably, however, absorbance may be measured by adding one or more wavelengths at which the difference in molar absorbance coefficient between the oxy-hemoglobin and the deoxy-hemoglobin is large, so that the measurement accuracy can be further improved. For example, the wavelength of 880 nm may be added, and the hemoglobin concentration and hemoglobin oxygen saturation calculated with the wavelengths of 950 and 810 nm substituted in the terms for the oxy-hemoglobin and the deoxy-hemoglobin, respectively, in the above equation can be averaged with the hemoglobin concentration and hemoglobin oxy-saturation calculated with 880 nm and 810 nm. In this way, the accuracy of measurement can be improved.

The combinations of the wavelengths are shown in Table 1.

TABLE 1

|  | 950 nm | 880 nm | 810 nm | 660 nm | 520 nm | 450 nm |
| --- | --- | --- | --- | --- | --- | --- |
| Case 1 | ○ |  | ○ |  |  | ○ |
| Case 2 | ○ | ○ | ○ |  |  | ○ |

TABLE 1-continued

|  | 950 nm | 880 nm | 810 nm | 660 nm | 520 nm | 450 nm |
| --- | --- | --- | --- | --- | --- | --- |
| Case 3 | ○ |  | ○ | ○ |  |  |
| Case 4 | ○ | ○ | ○ | ○ |  |  |
| Case 5 | ○ |  | ○ |  | ○ |  |
| Case 6 | ○ | ○ | ○ |  | ○ |  |
| Case 7 | ○ |  | ○ | ○ |  | ○ |
| Case 8 | ○ | ○ | ○ | ○ |  | ○ |
| Case 9 | ○ |  | ○ |  | ○ | ○ |
| Case 10 | ○ | ○ | ○ |  | ○ | ○ |
| Case 11 | ○ |  | ○ | ○ | ○ |  |
| Case 12 | ○ | ○ | ○ | ○ | ○ |  |
| Case 13 | ○ |  | ○ | ○ | ○ | ○ |
| Case 14 | ○ | ○ | ○ | ○ | ○ | ○ |

As shown in Table 1, the configuration of the apparatus can be modified depending on the desired accuracy using three to six wavelengths in combination. The wavelength 450 nm is related to the absorbance of bilirubin and may be omitted if it is expected that the measurement accuracy would not be greatly affected by bilirubin. The wavelength 520 nm is related to the absorbance of melanin. The wavelength 660 nm is related to the absorbance of turbidity in blood which mainly consists of cholesterol, neutral fat, and other substances causing hyperlipemia. In the case of subjects in which it is expected that the measurement accuracy would not be affected by these substances, one or the other of the wavelengths may be omitted.

Preferably, in addition to the wavelengths 950 nm and 810 nm for hemoglobin measurement, a third wavelength of 450 nm for bilirubin, 520 nm for melanin, or 660 nm for turbidity in blood may be added, for a total of three wavelengths. Generally, the wavelength 660 nm for blood turbidity is the most appropriate as the third wavelength; however, other wavelengths could be more effective depending on the characteristics of the group of subjects.

Preferably, the measurement may be made using two wavelengths selected from the group consisting of 450 nm for bilirubin, 520 nm for melanin and 660 nm for blood turbidity in addition to the wavelengths 950 nm and 810 nm for hemoglobin measurement, for a total of four wavelengths. As the two additional wavelengths, the 450 nm for bilirubin and the 660 nm for turbidity are generally most appropriate. However, other wavelengths could be more appropriate, depending on the characteristics of the group of subjects for measurement.

The measurement can also be made using five wavelengths of 950 nm and 810 nm for hemoglobin measurement, 450 nm for bilirubin, 520 nm for melanin, and 660 nm for turbidity in blood.

Preferably, in each of the cases of three, four, and five wavelengths, the wavelength 880 nm may be additionally used for the measurement of hemoglobin. By so doing, the oxy-hemoglobin and deoxy-hemoglobin concentrations determined from each combination of the wavelengths can be averaged with the oxy-hemoglobin and deoxy-hemoglobin concentrations determined by using 880 nm instead of 950 nm.

In the following embodiment, case 13 in Table 1 will be described.

Figure 9:
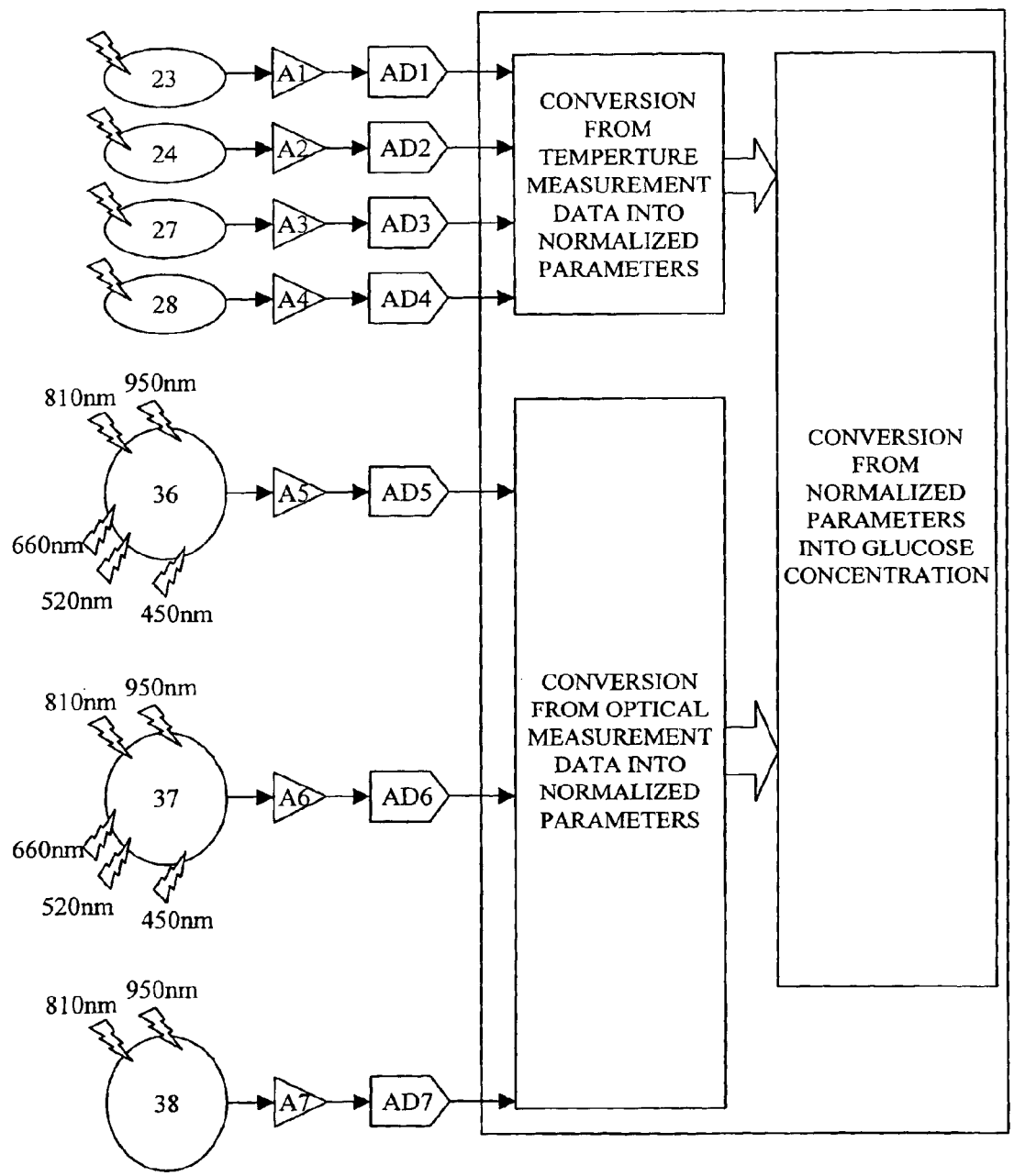
FIG. 9 shows a conceptual chart illustrating the flow of data processing in the apparatus.

FIG. 9 shows how data is processed in the apparatus. The apparatus according to the present example is equipped with thermistor 23, thermistor 24, pyroelectric detector 27, thermistor 28, and three photodetectors formed by photodiodes 36 to 38. The photodiodes 36 and 37 measure absorbance at wavelengths 810 nm, 950 nm, 660 nm, 520 nm, and 450 nm. The photodiode 38 measures the intensity of wavelengths 810 nm and 950 nm. Thus, the apparatus is supplied with sixteen kinds of measurement values including temperature, heat, and optical measurement data. In the case where the wavelength 880 nm is added for improving accuracy, the number of measurement values fed to the apparatus would be 19.

The seven kinds of analog signals are supplied via individual amplifiers $A_1$ to $A_7$ to analog/digital converters $AD_1$ to $AD_7$, where they are converted into digital signals. Based on the digitally converted values, parameters $x_i$ (i=1, 2, 3, 4, 5) are calculated. The following are specific descriptions of $x_i$ (where $e_1$ to $e_5$ are proportionality coefficients):

Parameter proportional to heat radiation $$x_1 = e_1 \times (T_3)^4$$

Parameter proportional to heat convection $$x_2 = e_2 \times (T_4 - T_3)$$

Parameter proportional to hemoglobin concentration $$x_3 = e_3 \times ([Hb] + [HbO_2])$$

Parameter proportional to hemoglobin oxygen saturation $$x_4 = e_4 \times \left( \frac{[HbO_2]}{[Hb] + [HbO_2]} \right)$$

Parameter proportional to blood flow volume $$x_5 = a_5 \times \left( \frac{1}{t_{CONT} \times (S_1 - S_2)} \right)$$

Then, normalized parameters are calculated from mean values and standard deviations of $x_i$ obtained from actual data pertaining to large numbers of able-bodied people and diabetic patients. A normalized parameter $X_i$ (where i=1, 2, 3, 4, 5) is calculated from each parameter $x_i$ according to the following equation:

$$X_i = \frac{x_i - \bar{x}_i}{SD(x_i)}$$

where
$x_i$: parameter
$\bar{x}_i$: mean value of the parameter
$SD(x_i)$: standard deviation of the parameter Using the above five normalized parameters, calculations are conducted for conversion into glucose concentration to be eventually displayed. A program necessary for the processing calculations is stored in a ROM in the microprocessor built inside the apparatus. The memory area required for the processing calculations is ensured in a RAM similarly built inside the apparatus. The results of calculation are displayed on the LCD.

The ROM stores, as a constituent element of the program necessary for the processing calculations, a function for determining glucose concentration C in particular. The function is defined as follows. C is expressed by the below-indicated equation (1), where as (i=0, 1, 2, 3, 4, 5) is determined from a plurality of pieces of measurement data in advance according to the following procedure:

(1) A multiple regression equation that indicates the relationship between the normalized parameters and the glucose concentration C is created.
(2) Normalized equations (simultaneous equations) relating to the normalized parameters are obtained from equations obtained by the least-squares method.
(3) Values of coefficient as (i=0, 1, 2, 3, 4, 5) are determined from the normalized equations and then substituted into the multiple regression equation.

Initially, the regression equation (1) indicating the relationship between the glucose concentration C and the normalized parameters $X_1$, $X_2$, $X_3$, $X_4$, and $X_5$ is formulated.

$$C = f(X_1, X_2, X_3, X_4, X_5) = a_0 + a_1 X_1 + a_2 X_2 + a_3 X_3 + a_4 X_4 + a_5 X_5 \quad (1)$$

Then, the least-squares method is employed to obtain a multiple regression equation that would minimize the error with respect to a measured value Ci of glucose concentration according to an enzyme electrode method. When the sum of squares of the residual is D, D is expressed by the following equation (2):

$$D = \sum_{i=1}^{n} d_i^2 \quad (2)$$

$$= \sum_{i=1}^{n} (C_i - f(X_{i1}, X_{i2}, X_{i3}, X_{i4}, X_{i5}))^2$$

$$= \sum_{i=1}^{n} \{C_i - (a_0 + a_1 X_{i1} + a_2 X_{i2} + a_3 X_{i3} + a_4 X_{i4} + a_5 X_{i5})\}^2$$

The sum of squares of the residual D becomes minimum when partial differentiation of equation (2) with respect to $a_0, a_2, \ldots, a_5$ gives zero. Thus, we have the following equations:

$$\frac{\partial D}{\partial a_0} = -2 \sum_{i=1}^{n} C_i - \quad (3)$$
$$\{(a_0 + a_1 X_{i1} + a_2 X_{i2} + a_3 X_{i3} + a_4 X_{i4} + a_5 X_{i5})\}$$
$$= 0$$

$$\frac{\partial D}{\partial a_1} = 2 \sum_{i=1}^{n} X_{i1} \{C_i -$$
$$(a_0 + a_1 X_{i1} + a_2 X_{i2} + a_3 X_{i3} + a_4 X_{i4} + a_5 X_{i5})\}$$
$$= 0$$

$$\frac{\partial D}{\partial a_2} = 2 \sum_{i=1}^{n} X_{i2} \{C_i -$$
$$(a_0 + a_1 X_{i1} + a_2 X_{i2} + a_3 X_{i3} + a_4 X_{i4} + a_5 X_{i5})\}$$
$$= 0$$

$$\frac{\partial D}{\partial a_3} = -2 \sum_{i=1}^{n} X_{i3} \{C_i -$$
$$(a_0 + a_1 X_{i1} + a_2 X_{i2} + a_3 X_{i3} + a_4 X_{i4} + a_5 X_{i5})\}$$
$$= 0$$

$$\frac{\partial D}{\partial a_4} = 2 \sum_{i=1}^{n} X_{i4} \{C_i -$$
$$(a_0 + a_1 X_{i1} + a_2 X_{i2} + a_3 X_{i3} + a_4 X_{i4} + a_5 X_{i5})\}$$
$$= 0$$

$$\frac{\partial D}{\partial a_5} = -2 \sum_{i=1}^{n} X_{i5} \{C_i -$$
$$(a_0 + a_1 X_{i1} + a_2 X_{i2} + a_3 X_{i3} + a_4 X_{i4} + a_5 X_{i5})\}$$
$$= 0$$

When the mean values of C and $X_1$ to $X_5$ are $C_{mean}$ and $X_{1mean}$ to $X_{5mean}$, respectively, since $X_{imean}=0$ (i=1 to 5), equation (1) provides:

$$a_0 = C_{mean} - a_1 X_{1mean} - a_2 X_{2mean} - a_3 X_{3mean} - a_4 X_{4mean} - a_5 X_{5mean} = C_{mean} \quad (4)$$

The variation and covariation between the normalized parameters are expressed by equation (5). Covariation between the normalized parameter $X_i$ (i=1 to 5) and C is expressed by equation (6).

$$S_{ij} = \sum_{k=1}^{n}(X_{ki} - X_{imean})(X_{kj} - X_{jmean}) = \sum_{k=1}^{n} X_{ki}X_{kj} \quad (5)$$

$$(i, j = 1, 2, \ldots 5)$$

$$S_{iC} = \sum_{k=1}^{n}(X_{ki} - X_{imean})(C_k - C_{mean}) = \sum_{k=1}^{n} X_{ki}(C_k - C_{mean}) \quad (6)$$

$$(i = 1, 2, \ldots 5)$$

Substituting equations (4), (5), and (6) into equation (3) and rearranging yields a set of simultaneous equations (normalized equations) (7). Solving the set of equations (7) yields $a_1$ to $a_5$.

$$a_1 S_{11} + a_2 S_{12} + a_3 S_{13} + a_4 S_{14} + a_5 S_{15} = S_{1C}$$

$$a_1 S_{21} + a_2 S_{22} + a_3 S_{23} + a_4 S_{24} + a_5 S_{25} = S_{2C}$$

$$a_1 S_{31} + a_2 S_{32} + a_3 S_{33} + a_4 S_{34} + a_5 S_{35} = S_{3C}$$

$$a_1 S_{41} + a_2 S_{42} + a_3 S_{43} + a_4 S_{44} + a_5 S_{45} = S_{4C}$$

$$a_1 S_{51} + a_2 S_{52} + a_3 S_{53} + a_4 S_{54} + a_5 S_{55} = S_{5C} \quad (7)$$

Constant term $a_0$ is obtained by means of equation (4). The thus obtained $a_i$ (i=0, 1, 2, 3, 4, 5) is stored in ROM at the time of manufacture of the apparatus. In actual measurement using the apparatus, the normalized parameters $X_1$ to $X_5$ obtained from the measured values are substituted into regression equation (1) to calculate the glucose concentration C.

Hereafter, an example of the process of calculating parameter Xi will be described. The example concerns measurement values obtained from a physically unimpaired person. Coefficients for the parameter calculation equations are determined by temperature data and optical measurement data that have been measured in advance. The ROM in the microprocessor stores the following formula for the calculation of the parameter:

$$x_1 = 0.98 \times 10^{-3} \times (T_3)^4$$

$$x_2 = 1.24 \times (T_4 - T_3)$$

$$x_3 = 1.36 \times ([Hb] + [HbO_2])$$

$$x_4 = 2.67 \times \left(\frac{[HbO_2]}{[Hb] + [HbO_2]}\right)$$

$$x_5 = 1.52 \times 10^6 \times \left(\frac{1}{t_{CONT} \times (S_1 - S_2)}\right)$$

When $T_3 = 36.5°$ C. is substituted in the above equations as a measurement value, for example, $x_1 = 1.74 \times 10^3$. When $T_4 = 19.7°$ C. is substituted in the above equations, $x_2 = 2.08 \times 10$. Then, before finding $x_3$, it is necessary to find [Hb] and [HbO$_2$]. The coefficients for the concentration calculation formula are determined by the scattered-light absorbance coefficient of each substance that has been measured in advance. Using that equation, [Hb] and [HbO$_2$] can be determined by solving the following set of simultaneous equations in the case of measurement using five wavelengths:

$$A_{D2\_450} = 9.74 \times 10^1$$
$$= 0.87\{60,000 \times [Hb] + 60,000 \times [HbO_2] + 55,000 \times [Bi] +$$
$$160 \times [Tur] + 1,900 \times [me]\} \times 0.93 \times 0.85$$

$$A_{D2\_520} = 4.90 \times 10$$
$$= 0.87\{33,000 \times [Hb] + 30,000 \times [HbO_2] + 54 \times [Bi] +$$
$$130 \times [Tur] + 1,300 \times [me]\} \times 0.93 \times 0.85$$

$$A_{D2\_660} = 1.40$$
$$= 0.87\{3,000 \times [Hb] + 300 \times [HbO_2] + 30 \times [Bi] +$$
$$100 \times [Tur] + 470 \times [me]\} \times 0.93 \times 0.85$$

$$A_{D2\_810} = 1.67$$
$$= 0.87\{800 \times [Hb] + 800 \times [HbO_2] + 3 \times [Bi] +$$
$$60 \times [Tur] + 190 \times [me]\} \times 0.93 \times 0.85$$

$$a_{Rough} = 0.85$$
$$= \frac{1.35 \times (9.74 \times 10^1 + 4.90 \times 10 + 1.40 + 1.67 + 1.98)}{(1.55 \times 10^1 + 7.78 \times 10 + 2.22 + 2.65 + 3.14)}$$

$$D = 0.93$$
$$= \frac{1}{\frac{1.06 \times (1.02 + 1.01)}{2}}$$

Solving this set of simultaneous equations gives [Hb]=0.09 mmol/L and [HbO$_2$]=2.21 mmol/L. Thus we have $x_3 = 3.13$ and $x_4 = 2.57$. Then, substituting $S_1 = 1.76 \times 10^2$, $S_2 = 1.89 \times 10$, and $t_{CONT} = 22$ seconds gives $x_5 = 4.40 \times 10^2$.

Similarly, in the case of using the four wavelengths 950 nm, 810 nm, 660 nm, and 450 nm at the same time, we have the following set of simultaneous equations:

$$A_{D2\_450} = 9.74 \times 10^1$$
$$= 0.87\{60,000 \times [Hb] + 60,000 \times [HbO_2] + 53,000 \times [Bi] +$$
$$190 \times [Tur]\} \times 0.93 \times 0.85$$

$$A_{D2\_660} = 1.40$$
$$= 0.87\{3,000 \times [Hb] + 300 \times [HbO_2] + 30 \times [Bi] + 146 \times$$
$$[Tur]\} \times 0.93 \times 0.85$$

$$A_{D2\_810} = 1.67$$
$$= 0.87\{800 \times [Hb] + 800 \times [HbO_2] + 3 \times [Bi] + 78 \times$$
$$[Tur]\} \times 0.93 \times 0.85$$

$$A_{D2\_950} = 1.98$$
$$= 0.87\{750 \times [Hb] + 1,150 \times [HbO_2] + 2 \times [Bi] + 34 \times$$
$$[Tur]\} \times 0.93 \times 0.85$$

$$a_{Rough} = 0.85$$
$$= \frac{1.35 \times (9.74 \times 10^1 + 1.40 + 1.67 + 1.98)}{(1.55 \times 10^1 + 2.22 + 2.65 + 3.14)}$$

$$D = 0.93$$
$$= \frac{1}{\frac{1.06 \times (1.02 + 1.01)}{2}}$$

where the absorbance coefficients in each equation are different from those in the case of five wavelengths. This is due to the fact that the influence of melanin is replaced with that of another substance in the mathematic expressions because of the absence of the wavelength of melanin.

Solving this set of simultaneous equations gives [Hb]=0.10 mmol/L and [HbO$_2$]=2.21 mmol/L.

Similarly, in the case of using the three wavelengths of 950 nm, 810 nm, and 660 nm at the same time, we have the following set of simultaneous equations:

$$A_{D2\_660} = 1.40$$
$$= 0.87\{3,000 \times [Hb] + 300 \times [HbO_2] + 140 \times [Tur]\} \times 0.93 \times 0.85$$

$$A_{D2\_810} = 1.67$$
$$= 0.87\{800 \times [Hb] + 800 \times [HbO_2] + 80 \times [Tur]\} \times 0.93 \times 0.85$$

$$A_{D2\_950} = 1.98$$
$$= 0.87\{750 \times [Hb] + 1,150 \times [HbO_2] + 34 \times [Tur]\} \times 0.93 \times 0.85$$

$$a_{Rough} = 0.85$$
$$= \frac{1.35 \times (1.40 + 1.67 + 1.98)}{(3.14 + 2.65 + 2.22)}$$

$$D = 0.93$$
$$= \frac{1}{\frac{1.06 \times (1.02 + 1.01)}{2}}$$

Solving this set of simultaneous equations gives [Hb]= 0.12 mmol/L and [HbO$_2$]=2.22 mmol/L.

Based on the results of detection by the five, four, and three wavelengths at the same time, the hemoglobin concentration ([Hb]+[HbO$_2$]) comes to 2.30 mmol/L, 2.31 mmol/L, and 2.34 mmol/L, respectively. The hemoglobin concentration was measured at the same time by an invasive method, namely by blood sampling, and the hemoglobin concentration turned out to be 2.28 mmol/L. These results show that the calculation result by the four wavelengths is closer to the hemoglobin concentration value obtained by blood sampling than by the three wavelengths, and that the calculation result by the five wavelengths is even closer to the actual value of the hemoglobin concentration than by the four wavelengths. The results thus indicate that accuracy of measurement can be increased by increasing the number of wavelengths used.

Next, $X_1$ to $X_5$ are obtained. $X_1$ to $X_5$ are the results of normalization of the above-obtained parameters $x_1$ to $x_5$. Assuming the distribution of the parameters is normal, 95% of the normalized parameter takes on values between –2 and +2. In Case 13 of Table 1, for example, the normalized parameters can be determined by the following equations:

$$X_1 = -0.06 = \frac{1.74 \times 10^3 - 1.75 \times 10^3}{167}$$

$$X_2 = 0.04 = \frac{2.08 \times 10 - 2.06 \times 10}{5}$$

$$X_3 = 0.05 = \frac{3.13 - 3.10}{0.60}$$

$$X_4 = -0.12 = \frac{2.54 - 2.60}{0.50}$$

$$X_5 = 0.10 = \frac{4.40 \times 10^2 - 4.52 \times 10^2}{120}$$

From the above equations, we have normalized parameters $X_1$=–0.06, $X_2$=+0.04, X3=+0.05, $X_4$=–0.12, and $X_5$=+0.10.

Hereafter, an example of the process of calculating the glucose concentration will be described. The coefficients in regression equation (1) are determined in advance based on many items of data obtained from able-bodied persons and diabetics, and the ROM in the microprocessor stores the following formula for calculating the glucose concentration:

$$C = 99.1 + 18.3 \times X_1 - 20.2 \times X_2 - 24.4 \times X_3 - 21.8 \times X_4 - 25.9 \times X_5$$

Substituting $X_1$ to $X_5$ gives C=96 mg/dl. In the case of a diabetic patient, substituting exemplary measurement values in the equation such that $X_1$=+1.15, $X_2$=–1.02, $X_3$=–0.83, $X_4$=–0.91, and $X_5$=–24 yields C=213 mg/dl.

Hereafter, the results of measurement by the conventional enzymatic electrode method and those by the method of the invention will be compared. In the enzymatic electrode method, a blood sample is reacted with a reagent and the amount of resultant electrons is measured to determine glucose concentration. When the glucose concentration for an able-bodied person was 89 mg/dl according to the enzymatic electrode method, the normalized parameters obtained by measurement at the same time according to the invention were $X_1$=–0.06, $X_2$=+0.04, $X_3$=+0.07, $X_4$=–0.10, and $X_5$=+0.10. Substituting these values the above equation yields C=95 mg/dl. On the other hand, when the glucose concentration for a diabetic patient was 238 mg/dl according to the enzymatic electrode method, the normalized parameters obtained by measurement at the same time according to the invention were $X_1$=+1.15, $X_2$=–1.02, $X_3$=–0.95, $X_4$=–1.05, and $X_5$=–1.24. Substituting these values into the above equation yields C=218 mg/dl. The results thus indicated that the method according to the invention can provide highly accurate glucose concentration.

Figure 10:
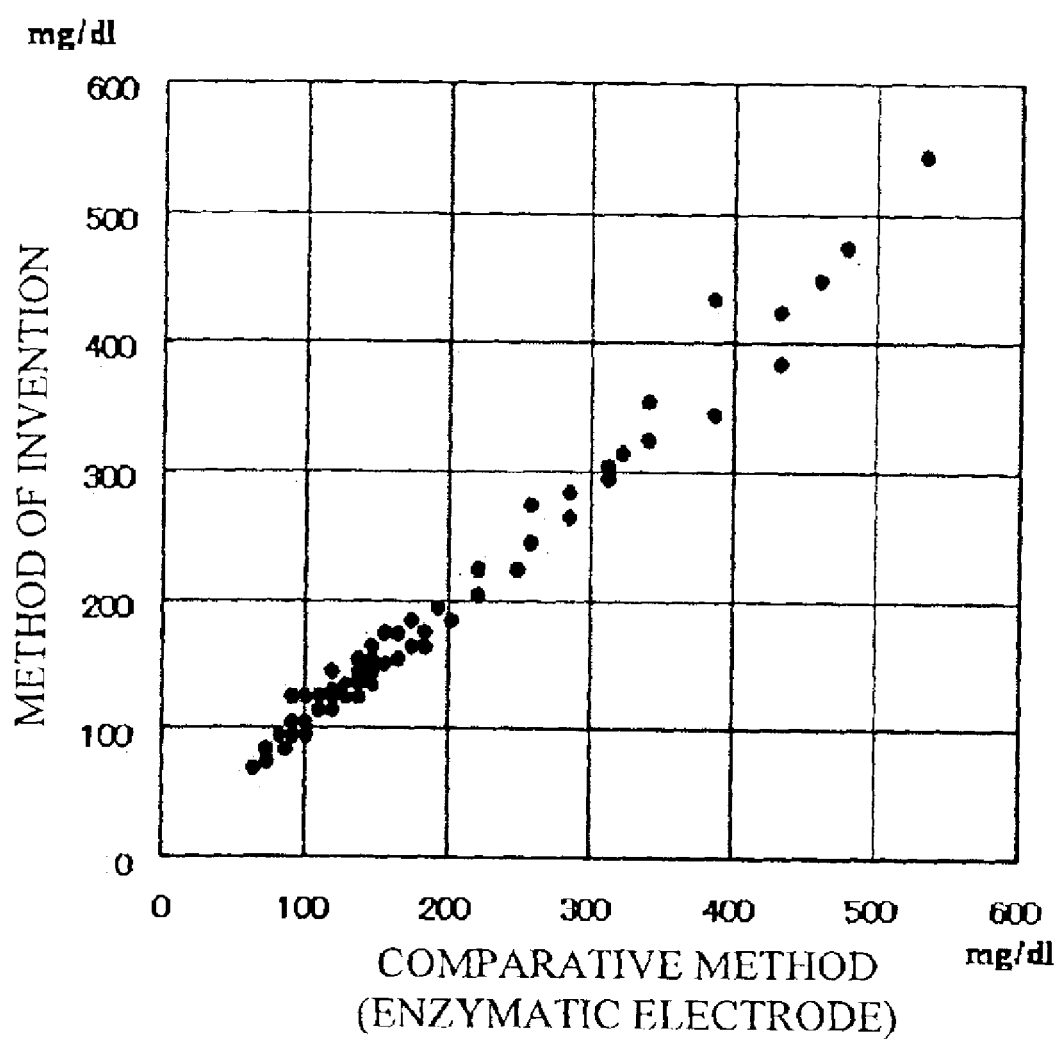
FIG. 10 shows the plots of the glucose concentration values calculated according to the present invention and the glucose concentration values measured by the enzymatic electrode method.

FIG. 10 shows the plot of glucose concentration for a plurality of patients. The calculated values of glucose concentration according to the invention are shown on the vertical axis, and the measured values of glucose concentration according to the enzymatic electrode method are shown on the horizontal axis. It will be seen that a good correlation can be obtained by measuring the oxygen supply volume and the blood flow volume according to the method of the invention (correlation coefficient=0.9434).

Thus, the invention can provide a highly accurate non-invasive blood sugar level measuring apparatus and method.

What is claimed is:

1. A blood sugar level measuring apparatus comprising:
   (1) a heat amount measuring unit for measuring a plurality of temperatures derived from a body surface in order to obtain information used for calculating the amount of convective heat transfer and the amount of radiation heat transfer concerning the dissipation of heat from the body surface;
   (2) a blood flow volume measuring unit for obtaining information concerning the volume of blood flow, the blood flow volume measuring unit comprising a body-surface contact unit, an adjacent-temperature detector disposed adjacent to the body-surface contact unit, an indirect-temperature detector for detecting the temperature at a position distanced away from the body-surface contact unit, and a heat conducting member connecting the body-surface contact unit with the indirect-temperature detector;
   (3) an optical measuring unit for obtaining the hemoglobin concentration and hemoglobin oxygen saturation in blood, the unit including a light source for generating light of at least three different wavelengths, an optical system for irradiating the body surface with light emitted by the light source, and at least three different photodetectors for detecting the light that has been shone on the body surface;
   (4) a storage unit for storing relationships between individual parameters corresponding to the plurality of temperatures, blood flow volume, hemoglobin concentration and hemoglobin oxygen saturation in blood, and blood sugar levels;
   (5) a computing unit for converting measurement values provided by the heat amount measuring unit, the blood flow volume measuring unit, and the optical measuring unit into parameters, and computing a blood sugar level by applying the parameters to the relationships stored in the storage unit; and (6) a display unit for displaying the blood sugar level computed by the computing unit.

2. The blood sugar level measuring apparatus according to claim 1, the photodetectors include a first photodetector for detecting light reflected by the body surface, a second photodetector for detecting light scattered by the body surface, and a third photodetector for detecting light that has penetrated into the skin through the body surface and that has exited from the body surface.

3. The blood sugar level measuring apparatus according to claim 2, wherein the light source comprises a plurality of light-emitting diodes that emit light with different wavelengths, and wherein the optical system includes a first optical fiber for transmitting the light emitted by the light-emitting diodes to an irradiated portion on the body surface, and a second optical fiber for transmitting the light with which the body surface has been irradiated to the first, second and third photodetectors.

4. The blood sugar level measuring apparatus according to claim 3, wherein the tip of the optical fiber transmitting the light to the third photodetector is disposed at a location so as to be in contact with the body surface when in use.

5. The blood sugar level measuring apparatus according to claim 2, wherein the light source produces light of a wavelength at which the molar absorbance coefficients of the oxy-hemoglobin and deoxy-hemoglobin are equal, light of a first wavelength for detecting the difference in absorbance between the oxy-hemoglobin and deoxy-hemoglobin, and light of a wavelength that is absorbed by bilirubin.

6. The blood sugar level measuring apparatus according to claim 5, wherein light is produced that has a wavelength that is absorbed by turbidity in blood or by melanin pigment.

7. The blood sugar level measuring apparatus according to claim 5 or 6, wherein light of a second wavelength is produced for detecting the difference in absorbance between the oxy-hemoglobin and deoxy-hemoglobin.

8. The blood sugar level measuring apparatus according to claim 5, wherein the light of the individual wavelengths with which the body surface has been irradiated is detected by the second photodetector.

9. The blood sugar level measuring apparatus according to claim 8, wherein the computing unit corrects measurement errors due to the body surface roughness using a ratio of the absorbance measured by the first photodetector and that measured by the second photodetector.

10. The blood sugar level measuring apparatus according to claim 8, wherein the computing unit corrects measurement errors due to skin thickness using the intensity of light measured by the third detector.

11. The blood sugar level measuring apparatus according to claim 10, wherein the computing unit makes the correction by taking a ratio between the absorbance of light that has entered a standard substance with a known thickness and that has exited therefrom as measured in advance by the third detector and the absorbance measured by the third detector.

12. The blood sugar level measuring apparatus according to claim 2, wherein the light that has penetrated into the skin via the body surface and that has exited via the body surface is transmitted from an exit portion to the third photodetector via an optical path with light-blocking surroundings.

13. The blood sugar level measuring apparatus according to claim 1, wherein the heat amount measuring unit comprises an ambient temperature detector for measuring the ambient temperature, and a radiation heat detector for measuring the heat radiated from the body surface.

14. The blood sugar level measuring apparatus according to claim 1, wherein the computing unit estimates the blood flow volume by measuring the amount of heat transfer from the body surface to the heat conducting member by monitoring a chronological variation of the temperatures detected by the adjacent-temperature detector and the indirect-temperature detector, and estimates the blood flow volume based on the amount of heat transfer.

15. A blood sugar level measuring apparatus comprising:
an ambient temperature detector for measuring the ambient temperature;
a body-surface contact unit to be brought into contact with a body surface;
a radiation temperature detector for measuring the radiation heat from the body surface;
an adjacent-temperature detector disposed adjacent to the body-surface contact unit;
an indirect-temperature detector for detecting the temperature at a position distanced away from the body-surface contact unit;
a heat conducting member connecting the body-surface contact unit with the indirect-temperature detector;
a light source for producing light of at least three different wavelengths consisting of 810 nm, 950 nm, and a third wavelength;
an optical system for irradiating the body surface with the light emitted by the light source;
at least three different photodetectors for detecting the light with which the body surface has been irradiated;
a storage unit for storing the relationships between individual outputs from the ambient temperature detector, radiation temperature detector, adjacent-temperature detector, indirect-temperature detector and the at least three different photodetectors, and blood sugar levels;
a computing unit for calculating a blood sugar level using the individual outputs with reference to made to the relationships stored in the storage unit; and
a display unit for displaying the blood sugar level calculated by the computing unit.

16. The blood sugar level measuring apparatus according to claim 15, wherein the third wavelength is selected from the group consisting of 450 nm, 660 nm, 520 nm, and 880 nm.

17. The blood sugar level measuring apparatus according to claim 15, wherein the light source produces light of a fourth wavelength which is used in combination with the third wavelength, wherein the two wavelengths to be combined are selected from the group consisting of 450 nm, 660 nm, 520 nm, and 880 nm.

18. The blood sugar level measuring apparatus according to claim 15, wherein the light source produces light of a fourth and a fifth wavelength which are used in combination with the third wavelength, wherein the three wavelengths to be combined are selected from the group consisting of 450 nm, 660 nm, 520 nm, and 880 nm.

19. The blood sugar level measuring apparatus according to claim 15, wherein at least one of the photodetectors detects light that has penetrated into the skin through the body surface and that has exited from an exit portion via an optical path having light-blocking surroundings.

* * * * *